United States Patent
Xia et al.

(10) Patent No.: US 8,542,955 B2
(45) Date of Patent: Sep. 24, 2013

(54) GAS DETECTION SYSTEM INCORPORATING FIBER GAS SENSORS HAVING FIBER BRAGG GRATINGS

(75) Inventors: Hua Xia, Niskayuna, NY (US); Renato Guida, Niskayuna, NY (US); Juntao Wu, Niskayuna, NY (US); Axel Busboom, Bavaria, DE (US); Aniceto Bantug, Clifton Park, NY (US); Pramod Chamarthy, Niskayuna, NY (US)

(73) Assignee: General Electric Company, Niskayuna, NY (US)

(*) Notice: Subject to any disclaimer, the term of this patent is extended or adjusted under 35 U.S.C. 154(b) by 427 days.

(21) Appl. No.: 12/913,950

(22) Filed: Oct. 28, 2010

(65) Prior Publication Data

US 2012/0103066 A1    May 3, 2012

(51) Int. Cl.
  *G02B 6/00* (2006.01)
  *G01N 25/00* (2006.01)

(52) U.S. Cl.
  USPC ............................... 385/12; 73/25.01

(58) Field of Classification Search
  USPC .................... 385/12, 13; 73/25.01
  See application file for complete search history.

(56) References Cited

U.S. PATENT DOCUMENTS

| | | | |
|---|---|---|---|
| 5,218,347 A | 6/1993 | Deppe | |
| 5,767,411 A * | 6/1998 | Maron | 73/705 |
| 6,712,770 B2 | 3/2004 | Lin et al. | |
| 7,140,232 B2 | 11/2006 | Wright et al. | |
| 7,151,872 B1 | 12/2006 | Xia et al. | |
| 7,489,835 B1 * | 2/2009 | Xia et al. | 385/12 |
| 7,567,734 B2 | 7/2009 | Dai et al. | |
| 2004/0234221 A1 * | 11/2004 | Kringlebotn et al. | 385/128 |
| 2005/0163424 A1 | 7/2005 | Chen | |
| 2006/0215959 A1 | 9/2006 | McCarthy et al. | |
| 2008/0218758 A1 | 9/2008 | Xia et al. | |
| 2008/0219618 A1 | 9/2008 | McCarthy et al. | |
| 2009/0041405 A1 * | 2/2009 | Dai et al. | 385/12 |

(Continued)

FOREIGN PATENT DOCUMENTS

| | | |
|---|---|---|
| EP | 1705462 A2 | 9/2006 |
| GB | 2430027 A | 3/2007 |

(Continued)

OTHER PUBLICATIONS

M. Buric, K. P. Chen, M. Bhattarai, P. R. Swinehart, M. Maklad, "Active fiber Bragg grating hydrogen sensors for all-temperature operation," IEEE Photonics Technology Letters, vol. 19, No. 5, pp. 255-257, Mar. 1, 2007.*

Search Report from corresponding GB Application No. GB1118484.3 dated Feb. 2, 2012.

(Continued)

*Primary Examiner* — Lisa Caputo
*Assistant Examiner* — Punam Roy
(74) *Attorney, Agent, or Firm* — Ann M. Agosti

(57) ABSTRACT

A gas detection system is provided for identifying a gas. The gas detection system includes a sensing module with a hollow chamber enclosed by a chamber housing. Additionally, the sensing module includes an optical sensing fiber positioned within the hollow chamber. The optical sensing fiber includes a gas sensor including a fiber Bragg grating positioned at a grating location along the optical sensing fiber, and a sensing layer affixed to an exterior surface of the optical sensing fiber at the grating location. After the gas is directed into the hollow chamber, the sensing layer and the gas exchange heat energy, based in part on a heat transfer coefficient of the gas. The exchange of the heat energy induces a shift in a Bragg resonant wavelength of the fiber Bragg grating which exceeds a threshold shift required for detection, where the shift is used to identify the gas.

9 Claims, 9 Drawing Sheets

(56) References Cited

U.S. PATENT DOCUMENTS

| | | | |
|---|---|---|---|
| 2009/0129721 A1* | 5/2009 | Chen et al. | 385/12 |
| 2011/0228275 A1* | 9/2011 | Xia et al. | 356/437 |
| 2013/0022308 A1* | 1/2013 | Wild et al. | 385/12 |

FOREIGN PATENT DOCUMENTS

| | | |
|---|---|---|
| WO | 2008125686 A1 | 10/2008 |
| WO | WO 2008/136870 A2 | 11/2008 |
| WO | WO 2008/136870 A3 | 11/2008 |

\* cited by examiner

GAS DETECTION SYSTEM INCORPORATING FIBER GAS SENSORS HAVING FIBER BRAGG GRATINGS

BACKGROUND OF THE INVENTION

In a variety of applications in which a gas is present, it may be necessary to know the identity of the gas. For example, a hydrogen-cooled generator typically uses a high purity of hydrogen gas which flows within sealed chambers of the generator for maintaining power generation efficiency. However, a small amount of air may penetrate the sealed chamber of the generator. Thus, a gas analyzer may be needed, to determine the hydrogen gas purity within the generator, to ensure that the purity of hydrogen gas is within a concentration range, such as 95-98%, for example. In the event that the generator encounters an operating problem, it may be necessary to open a generator case, in order to troubleshoot the problem. However, the generator case initially contains pure hydrogen gas, and may cause a safety hazard if the case was prematurely opened. Thus, a secondary gas such as carbon dioxide ($CO_2$) or nitrogen gas ($N_2$) may be used to purge the generator case until the relative concentration of hydrogen gas is less than a threshold concentration, such as 4%, for example, before the case can be safely opened. Thus, a gas analyzer may be needed, to determine the relative concentration of the secondary gas and the hydrogen gas within the generator case, in order to determine that the generator case can be safely opened during a shutdown time.

Various gas analytical techniques have been developed to analyze gas and gas compositions, such as infrared absorption and thermal conductivity detection. However, these conventional techniques have several drawbacks, such as not providing a single gas sensor which is capable of sensing a wide range of gases, thereby necessitating a separate sensor/system for different gases. Additionally, for example, infrared absorption is used to sense a limited amount of gases, such as hydrocarbon-based gases, but is incapable of sensing various common gases, such as hydrogen. Additionally, for example, a conventional thermal conductivity detection technique is used to sense certain gases, but is less accurate at sensing a wide range of gases, based on a lack of required thermal sensitivity and baseline drift.

Thus, it would be advantageous to provide a gas detection system which overcomes the noted drawbacks of conventional gas sensing technologies, and is conveniently capable of sensing a wide variety of gases, with the required sensitivity.

BRIEF DESCRIPTION OF THE INVENTION

In one embodiment in accordance with aspects of the present invention, a gas detection system is provided for identifying a gas. The gas detection system includes a sensing module with a hollow chamber enclosed by a chamber housing. Additionally, the sensing module includes an optical sensing fiber positioned within the hollow chamber. The optical sensing fiber includes a gas sensor including a fiber Bragg grating positioned at a grating location along the optical sensing fiber, and a sensing layer affixed to an exterior surface of the optical sensing fiber at the grating location. After the gas is directed into the hollow chamber, the sensing layer of the gas sensor and the gas exchange heat energy, based in part on a heat transfer coefficient of the gas. The exchange of the heat energy induces a shift in a Bragg resonant wavelength of the fiber Bragg grating of the gas sensor which exceeds a threshold shift required for detection, where the shift is used to identify the gas.

In another embodiment in accordance with aspects of the present invention, a gas detection system is provided for identifying a gas. The gas detection system includes an optical sensing fiber with a plurality of gas sensors, each gas sensor including a fiber Bragg grating positioned at a respective grating location along the optical sensing fiber and a sensing layer affixed to an exterior surface of the optical sensing fiber at each grating location. The sensing layer of each gas sensor is configured with a thermal sensitivity tuned to detect a gas with a heat transfer coefficient within a range. A respective exchange of heat energy between the a sensing layer and the gas within the heat transfer coefficient range induces a shift in the Bragg resonant wavelength at the respective grating location that exceeds a threshold shift required for detection of the gas within the range of the heat transfer coefficient.

In another embodiment in accordance with aspects of the present invention, a gas detection system is provided for identifying a gas. The gas detection system includes a hollow chamber enclosed by a chamber housing and configured to receive the gas. Additionally, the gas detection system includes an optical sensing fiber positioned within the hollow chamber. The optical sensing fiber includes a plurality of gas sensors, where each gas sensor includes a respective fiber Bragg grating positioned at a respective grating location along the optical sensing fiber, and a respective sensing layer affixed to an exterior surface of the optical sensing fiber at each grating location. The sensing layer of the gas sensor exchanges heat energy with the gas, based on a heat transfer coefficient of the gas and a temperature difference between the sensing layer and the gas. Additionally, the gas detection system includes a photodetector to detect a respective shift in a Bragg resonant wavelength from each fiber Bragg grating of the gas sensor. The respective shift in the Bragg resonant wavelength is induced by the respective heat energy dissipated by each sensing layer of the gas sensor to the gas. Additionally, the gas detection system includes a controller coupled to the photodetector, to identify the gas, based on the respective shift in the Bragg resonant wavelength from each fiber gas sensor.

DETAILED DESCRIPTION

Figure 1:
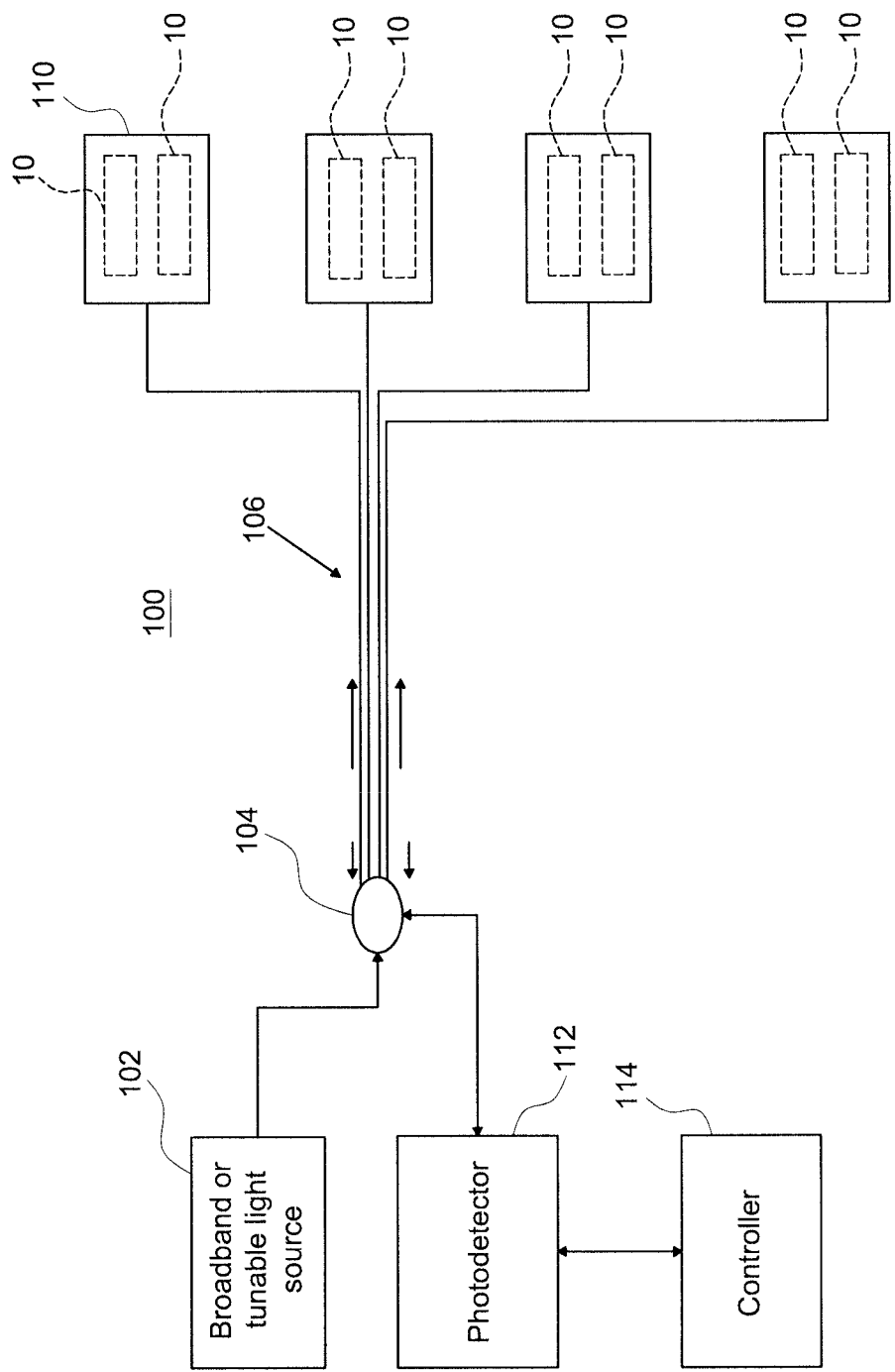
FIG. 1 is a block diagram of an exemplary embodiment of a thermal convective gas detection system for identifying a gas in accordance with aspects of the present invention.

Aspects of the present invention discuss the sensing and identification of a gas and gas composition, including a multiple single-component pure gas, a two-component binary gas (a gas mixture of two pure gases), or a multi-component gas or multi-gas (a gas mixture of more than two pure gases). For example, if a pure gas is input into the sensor system, an identification of the gas, such as $H_2$ gas or $N_2$ gas, will be determined, based on a wavelength shift from a fiber gas sensor (FGS). In another example, if a binary gas is input into the sensor system, an identification of each pure gas within the binary gas, as well as the relative concentrations of each pure gas will be provided, such as 96% $CO_2$ and 4% $H_2$, for example. In an exemplary embodiment, for a binary gas formed from a first and second single-component gas, the first single-component gas may induce a wavelength shift of $\Delta\lambda_1$, and the second single-component gas may induce a wavelength shift of $\Delta\lambda_2$, while the binary gas itself induces a wavelength shift of $\Delta\lambda$. If $\Delta\lambda_1 > \Delta\lambda_2$, then the first single-component gas concentration within the binary gas, in percentage, is determined by:

$$C(1) = \frac{\Delta\lambda - \Delta\lambda_2}{\Delta\lambda_1 - \Delta\lambda_2} * 100(\%) \quad (1)$$

where $\Delta\lambda_1 - \Delta\lambda_2$ is the gas sensor dynamic range. A gas sensor sensitivity may be expressed as the wavelength response/shift amplitude for each 1% gas concentration variation.

As discussed above, conventional thermal conductivity gas detection technology lacks the necessary sensitivity and accuracy to detect a wide variety of gases, including pure gases, binary gases and multi-gases. The inventors have developed a gas detection system which utilizes a thermal convective effect to identify a gas or gas composition, based on the range of gases which are adapted to be used for a particular application, such that the gas detection system is designed to have the necessary sensitivity for each gas. Since the thermal convective effect induced energy exchange between the fiber gas sensor and the gas stream is based on the gas specific heat capacity, gas thermal conductivity coefficient, and flow rate of the gas, the fiber gas sensor can be designed to respond to a specific range of gases.

As discussed in greater detail below, the gas detection system involves thermal convection through the exchange of thermal energy between the input gas and a fiber gas sensor. Specifically, the gas detection system may include multiple fiber gas sensors, which collectively include multiple sensing layers, and each of which is designed with a thermal sensitivity which is individually tuned to exchange thermal energy with a gas having a heat transfer coefficient within a respective range. Thus, for example, a first sensing layer of a first fiber gas sensor may be designed with a first thermal sensitivity, in order to exchange thermal energy with a gas having a high heat transfer coefficient. In another example, a second sensing layer of a second fiber gas sensor may be designed with a second thermal sensitivity, in order to exchange thermal energy with a gas having a low heat transfer coefficient. Thus, in order to ensure that the gas detection system has adequate sensitivity for gases with a range of heat transfer coefficients, the gas detection system includes multiple gas sensors with multiple sensing layer materials, where each respective sensing layer of each gas sensor is configured to exchange thermal energy with a group of gases having a heat transfer coefficient within a respective range, such that the combination of the multiple gas sensors and multiple sensing layers within the gas detection system is capable of detecting and identifying a wide range of gases with a collectively wide range of heat transfer coefficient.

FIG. 1 illustrates a gas detection system 100 for identifying a gas and analyzing a gas composition, which may be a pure gas, a binary gas or a multi-gas. The gas detection system 100 includes a broadband optical source 102 which outputs an optical signal such as a laser, for example, into an optical coupler 104, which in-turn couples the optical signal into four separate fiber transmission cables 106. Each fiber transmission cable 106 transmits the optical signal to a respective sensing module housing 110, which encloses a pair of sensing modules 10. Although FIG. 1 illustrates that a pair of sensing modules 10 are enclosed by the housing 110, less or more than two sensing modules may be enclosed by the sensing module housing. The sensing module 10 is discussed below in the embodiment of FIG. 2. Additionally, the sensing module housing could be an explosive proven metallic enclosure. However, the sensing module housing need not be made from a metallic material. The pair of sensing modules 10 is positioned within the sensing module housing 110, to provide testing redundancy, so that at least one sensing module 10 provides data to identify the gas, in the event that the other sensing module 10 is inoperable. In an exemplary embodiment, in which a pair of sensing modules 10 is positioned within the sensing module housing 110, a timer controlled switcher may be used within the sensing module housing 110, to alternately direct the inlet gas into the sensing modules 10 at fixed time intervals, such as from an interval on the order of seconds to thirty minutes, for example. As discussed in greater detail below, the sensing module 10 responds to the gas stream induced thermal convective loss by shifting its resonant Bragg wavelength, where the relative wavelength shift is representative of the identity of the gas within the sensing module 10.

As further illustrated in FIG. 1, a photodetector or a multi-channel signal process unit 112 is provided for analyzing the shift in the wavelength of the optical signal from each sensing module 10. In an exemplary embodiment, the process unit 112 is a 1-16 channel multiplexer, where one channel may be utilized to analyze the spectrum of the wavelength shift from each sensing module 10. However, the embodiments are not limited to a 16 channel multiplexer and may use a 32 channel multiplexer or any channel multiplexer, based on the number of sensing modules 10. Additionally, although FIG. 1 illustrates four sensing modules 10 within the gas detection system 100, less or more than four sensing modules may be used within the system and thus the embodiments are not limited to any particular number of sensing modules. Additionally, a controller or processor 114 receives the analyzed spectral data from the signal process unit 112, to identify the gas within each sensing module 10. In an exemplary embodiment, the processor 114 may be controlled with a LabVIEW based software.

Figure 2:
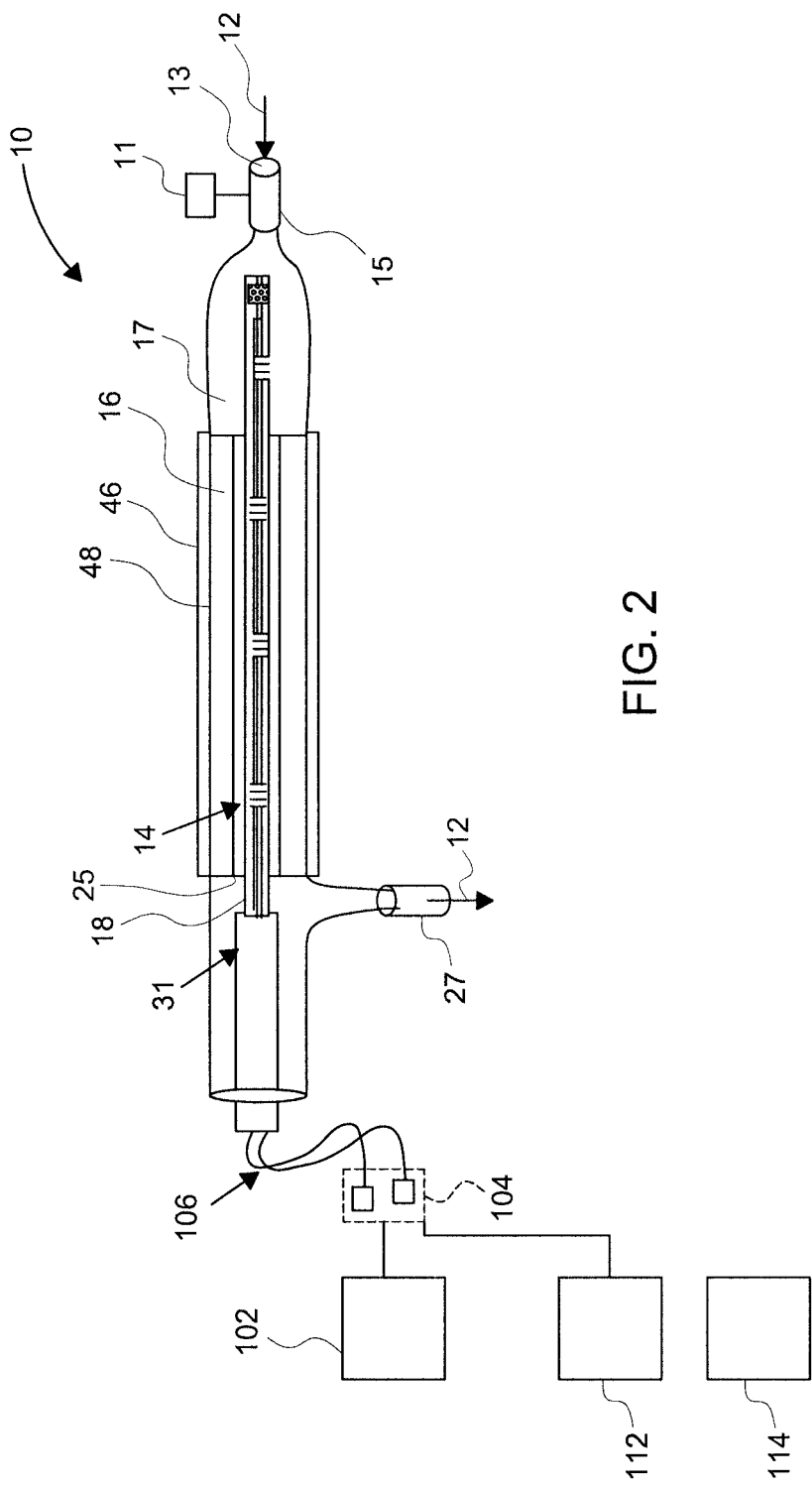
FIG. 2 is a side cross-sectional view of an exemplary embodiment of a sensing module illustrated in the sensor system of FIG. 1.

FIG. 2 illustrates the sensing module 10 for identifying a gas, which may be any of a pure gas, a binary gas and a multi-gas, for example. The embodiment of FIG. 2 may be considered as the gas detection system 100 of FIG. 1, where only one sensing module 10 is used within the gas detection system 100. The sensing module 10 includes a hollow chamber 14, which may be a hollow guide, enclosed by a chamber housing 16, which may be a double-wall housing, for example. In an exemplary embodiment, the chamber housing 16 is a cylindrical structure, which is made from a low-thermal-expansion material, such as fused quartz glass, for example. The double-wall intra-cavity may be sealed with dried air for mitigating thermal energy conduction as the gas passes through the hollow chamber 14. The sensing module 10 further includes the optical sensing fiber 18 which is positioned within the hollow chamber 14. As illustrated in FIG. 2, the optical sensing fiber 18 is positioned such that it is suspended within the hollow chamber 14 with a sensing rake 31, and the longitudinal axis of the optical sensing fiber 18 and the sensing rake 31 is coincident with the longitudinal axis of the hollow chamber 14. Although FIG. 2 shows a hollow chamber having a cylindrical shape with the optical sensing fiber positioned such that the longitudinal axis of the optical sensing fiber is coincident with the longitudinal axis of the hollow chamber, the embodiments of the present is not limited to this arrangement, provided that the sensing module is capable of identifying the gas using a thermal exchange between the gas and the fiber gas sensors, as discussed in greater detail below.

Figure 3:
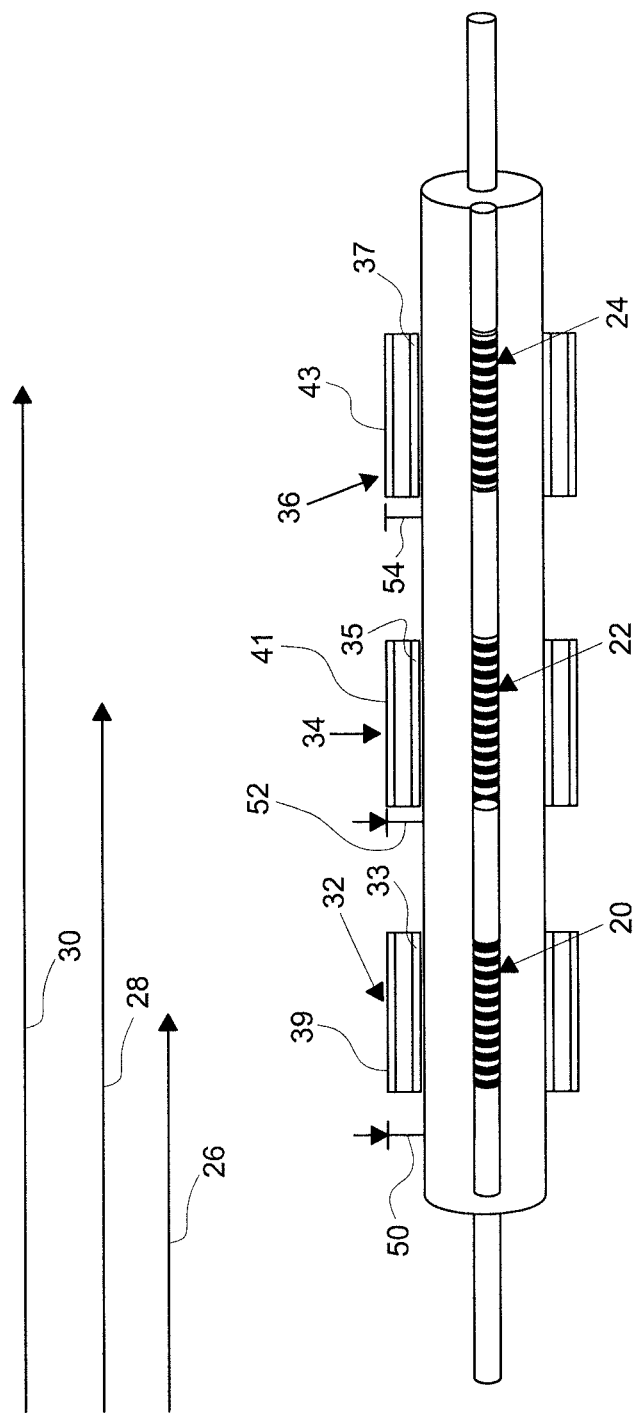
FIG. 3 is a partial-side cross-sectional view of the optical sensing fiber of the sensing module illustrated in FIG. 2.

FIG. 3 illustrates that the optical sensing fiber 18 positioned within the hollow chamber 14 includes three fiber gas sensors (FGS). Each of the three fiber gas sensors (FGS) include three respective fiber Bragg gratings 20,22,24 positioned at respective grating locations 26,28,30 along the optical sensing fiber 18 which are supported by the sensing rake 31. As appreciated by one of skill in the art, the fiber Bragg gratings are inscribed within the core of the photosensitive optical fiber 18, with conventional laser and phase mask techniques, and are surrounded by the cladding of the optical fiber. Additionally, as illustrated in FIG. 3, the three fiber gas sensors (FGS) include three respective sensing layers 32,34,36 affixed to an exterior surface 38 of the optical sensing fiber 18 (i.e., the cladding) at each respective grating location 26,28,30. Thus, each fiber gas sensor (FGS) includes a respective fiber Bragg grating positioned at a respective grating location, and a respective sensing layer affixed to an exterior surface of the optical sensing fiber at the respective grating location. In an exemplary embodiment of aspects of the present invention, the sensing layer 32,34,36 is bonded to the exterior surface 38, using a bonding layer 33,35,37, as discussed below. Although FIG. 3 illustrates three fiber Bragg gratings positioned within the optical sensing fiber 18, the embodiments are not limited to three fiber Bragg gratings, and may use less or more than three fiber Bragg gratings positioned within the optical sensing fiber 18, depending on the types of gases or gas compositions subject to identification, as discussed in further detail below. The selection of the number of fiber Bragg gratings to be positioned within the optical sensing fiber 18 is a consideration during a design phase of the sensing module 10, and is based on various factors, such as the range of gas composition to be detected, or the type of gas to be detected, for example. In an exemplary embodiment, the fiber Bragg gratings are inscribed in the single-mode fiber core with an apodized periodic modulated refractive index grating structure with the sensing layer surrounding its cladding.

As illustrated in FIG. 2, the sensing module 10 further includes a thermal stabilizer 46 attached to an exterior surface 48 of the chamber housing 16, which may be a double-wall chamber housing, as discussed above. The thermal stabilizer 46 is maintained at a first temperature or an operation temperature, such as 300° F., for example. The thermal stabilizer may be a heat-wrap blanket (which may be powered by a standard wall outlet) which is wrapped around the exterior surface of the chamber housing, which is made from a low-thermal-expansion material, such as a fused quartz tube. The chamber housing 16 is heated to the operation temperature, based on the attachment of the thermal stabilizer 46 to the exterior surface 48 of the chamber housing 16. The fiber Bragg gratings 20,22,24 and the sensing layers 32,34,36 are also heated to the operation temperature, based on a thermal convection heat transfer from the chamber housing 16 through the hollow chamber 14. As discussed above, in an exemplary embodiment, the chamber housing 16 may be made from thermal radiation limited material, such as a fused quartz material, which attenuates infrared radiation energy from the thermal stabilizer, to reduce sensor thermal noise at wavelengths greater than a threshold wavelength, such as 2 μm, for example. Thus, the chamber housing 16 is made from a material to ensure that the sensing layers 32,34,36 and the optical sensing fiber 18 are heated to the operation temperature by thermal convection.

The fiber Bragg gratings 20,22,24 and the optical sensing fiber 18 are supported by the sensing rake 31, which may be a quartz-rod-like rake. To ensure that the thermal energy exchange occurs between the sensing module 10 and the gas stream 12, the sensing rake 31 is provided with a cylindrical body with one or more openings such that each grating 20,22,24 is exposed to the gas stream while mitigating the possibility of thermal conduction from the sensing rake 31 to the fiber Bragg gratings 20,22,24. One end of the cylindrical body of the sensing rake 31 may be used to seal the hollow chamber 14, while the other end is suspended within the center of the hollow chamber 14. The inlet gas stream 12 can freely pass through the sensing rake 31, pass by the fiber Bragg gratings 20,22,24 and exit through the exhaust outlet 27. Based on the same consideration, to mitigate potential thermal radiation and conduction from the sensing rake 31 to the fiber Bragg gratings 20,22,24, and the different coefficients of thermal expansion which induce thermal stress, the sensing rake 31 material may be constructed with a fused quartz glass material.

As illustrated in FIG. 2, during the operation of the sensing module 10, the gas 12 is directed into an inlet 13 at an adjustable flowrate and through a thermal radiator 15, which acts as a heat-sink to reduce a temperature variation of the gas 12 to an inlet temperature or a second temperature (if the initial gas temperature is above the inlet temperature) before the gas 12 passes through a front hollow chamber 17 which is a single-wall chamber for reducing gas turbulence, before the gas 12 enters the hollow chamber 14. In an exemplary embodiment, the inlet temperature ranges from 0 to 100° F. The sensing module 10 includes a flowmeter 11 connected to the inlet 13, to adjust the flowrate of the gas 12 through the hollow chamber 14. Once the gas 12 enters the hollow chamber 14 at the inlet temperature, the sensing layer 32,34,36 at each grating location 26,28,30 respectively exchange heat energy with the gas 12, based in part on a heat capacity of the gas, and additionally on a thermal conductivity and expansion characteristic of a material of each sensing layer 32,34,36 and the temperature difference between the operation temperature of the sensing layer 32,34,36 and the initial inlet temperature of the gas 12. The respective exchange of the heat energy between each sensing layer 32,34,36 of each fiber gas sensor (FGS) and the gas 12 induces a shift in a Bragg resonant wavelength of each respective fiber Bragg grating 20,22, 24 among each fiber gas sensor (FGS) which is characteristic of the gas 12, and thus the sensing module 10 uses the shift in the Bragg resonant wavelength of each respective fiber Bragg grating 20,22,24, to identify the gas 12. After the gas 12 passes through the hollow chamber 14, it exits the fiber gas sensing module 10 through the outlet 27.

As illustrated in FIGS. 1 and 2, the sensing module 10 receives an optical signal from a broadband or tunable source 102 which is transmitted into an optical sensing fiber 106 using an optical coupler 104. As discussed above, the sensing module 10 illustrated in FIG. 2 may be considered as a special case of the gas detection system 100 of FIG. 1, in which a single sensing module 10 is utilized, for example. The light source 102 transmits a laser into the fiber cables 106, which then pass the laser into the sensing rake 31 and into the sensing module housing 16. As mentioned before, the sensing rake 31 is utilized to position the fiber Bragg gratings 20,22, 24 or fiber gas sensors within the hollow chamber 14 enclosed by the double-wall housing 16. Specifically, the sensing rake 31 includes one or more openings, which enable all of the fiber Bragg gratings 20,22,24 to be positioned within the gas flow path. In an exemplary embodiment, each optical sensing fiber 18 is secured to a V-groove and multiple optical sensing fibers or fiber Bragg grating arrays can be secured to parallel V-grooves. As appreciated by one of ordinary skill in the art, for each fiber Bragg grating 20,22,24, the light source 102 provides a respective broadband laser source or tunable light source, which is coupled from the optical coupler 104 in FIGS. 1-2 to the optical sensing fiber 106, to measure a respective shift of each respective Bragg resonant wavelength from each fiber Bragg grating 20,22,24 of each respective fiber gas sensor (FGS). Although FIG. 1 illustrates that the gas detection system 100 includes a single light source 102 and optical coupler 104 for multiple sensing modules 10, the embodiment of FIG. 2 discusses that a single light source 102 and the photodetector 112 or process unit 114 may be utilized with a single sensing module 10. The sensing module 10 also includes the controller or processor 114 that is coupled to the photodetector 112, where the photodetector 112 transmits the detected spectral data of the Bragg resonant wavelength shift to the processor 114. Based on the spectral data of the shift in the Bragg resonant wavelength from each respective fiber Bragg grating 20,22,24 of each fiber gas sensor (FGS), the processor 114, which may be a multi-channel signal process unit and data acquisition processor, for example, identifies the gas 12, by considering all of the respective shifts in the Bragg resonant wavelength from all of the fiber Bragg gratings 20,22,24 of all fiber gas sensors (FGS).

In an exemplary embodiment, the exchange of heat energy between the sensing layers 32,34,36 and the gas 12 is a dissipation of heat energy from the sensing layers 32,34,36 to the gas 12, by thermal convection. As appreciated by one of skill in the art, a dissipation of heat energy through thermal convection is directed from an area of higher temperature to an area of lower temperature and the rate of thermal convection is proportional to the difference in the temperature between the higher temperature and the lower temperature, as well as the heat conduction coefficients of the gas 12 and each sensing layer 32,34,36, as well as the chamber 14 geometry. As discussed above, the gas 12 is directed into the hollow chamber 14 at an initial inlet temperature, and the sensing layers 32,34,36 are at the operation temperature. The inlet temperature is different than the operation temperature, and more specifically, the inlet temperature is less than the operation temperature. In an exemplary embodiment, the operation temperature is set in the range from 200° F. to 300° F. and the inlet temperature is set in the range from 0° F. to 100° F. In an exemplary embodiment, the difference between the operation temperature and the inlet temperature during the operation of the sensing module 10 is at least 150° F. In an additional exemplary embodiment, the difference between the operation temperature and the inlet temperature during the operation of the sensing module 10 is at least 100° F.

As illustrated in FIG. 3, the sensing layers 32,34,36 of each fiber gas sensor (FGS) are respectively bonded to the exterior surface 38 (i.e., cladding) of the optical sensing fiber 18 at the respective grating locations 26,28,30 of each fiber gas sensor (FGS). A bonding layer 33,35,37 is provided between the sensing layers 32,34,36 and the exterior surface 38, to securely bond the respective sensing layers 32,34,36 to the exterior surface 38 of the optical sensing fiber 18. In an exemplary embodiment, the bonding layer is made from titanium, nickel, copper and/or chrome materials with a thickness in the range from 10 nm to 40 nm, for example. Additionally, as illustrated in FIG. 3, a capping layer or protection layer 39,41,43 is provided on an outside surface of the sensing layers 32,34,36, to protect the sensing layers 32,34,36 from oxidization or corrosion. In an exemplary embodiment, the protection layer is made from one of nickel, gold and/or chrome materials having a thickness of approximately 100 nm, for example. In an exemplary embodiment, the protection layer may be a chemically active layer that is made from a palladium alloy or copper oxide material for identifying hydrogen or hydrogen sulfide or may be made from a palladium doped tin oxide material for identifying methane or carbon monoxide, for example, and having a thickness from 10 nm to 50 nm, for example. Although FIG. 3 illustrates the protection layers 39,41,43 covering the outside surface of the sensing layers 32,34,36, the sensing module 10 may be operated without the use of the protection layers 39,41,43, provided that inert gases are being analyzed. In an exemplary embodiment, the sensing layer may be a chemically active layer and the fiber gas sensors may be operated without the use of the protection layers 39,41,43, provided that a multi-gas is being identified.

The temperature of the sensing layers 32,34,36 and the optical sensing fiber 18 will decrease from the operation temperature, as the gas 12 passes through the hollow chamber 14, based on the dissipation of the heat energy from the sensing layers 32,34,36, to the gas 12. The variation in the temperature of the sensing layers 32,34,36 will induce a respective strain reduction in the fiber Bragg gratings 20,22, 24 of each fiber gas sensor, based on a respective thermal expansion characteristic of the optical sensing fiber 18 and each material of the sensing layers 32,34,36. Since the thermal expansion characteristic of each sensing layer 32,34,36 is much greater than the thermal expansion characteristic of the fiber Bragg gratings 20,22,24, the temperature variation will induce a variation in the strain in the sensing layers 32,34,36 (compressed strain) than in the fiber Bragg gratings 20,22,24 (tensile strain), and thus will create an interface strain between the sensing layers 32,34,36 and the fiber Bragg grating 20,22,24. The respective strain of each sensing layer 32,34,36 is based on a respective thermal expansion characteristic of each material of the sensing layers 32,34,36 and a respective thickness 50,52,54 of each sensing layer 32,34,36. The respective strain of each sensing layer 32,34,36 induces a respective shift in the Bragg resonant wavelength of each respective fiber Bragg grating 20,22,24 of each fiber gas sensor, which is represented as:

$$\Delta\lambda = \lambda_B \cdot \xi \cdot (\alpha_m - \alpha_f) \cdot \Delta T + \lambda_B \cdot (\alpha_f + \beta) \cdot \Delta T$$

$$\Delta\lambda = (\kappa_\epsilon + \kappa_T) \cdot \Delta T \quad (2)$$

where $\Delta\lambda$ is the shift in the Bragg resonant wavelength of each respective fiber Bragg grating 20,22,24; $\lambda_B$ is the initial Bragg resonant wavelength; $\xi$ is a parameter proportional to the thickness 50,52,54 of each sensing layer 32,34,36, Young's modulus and Poisson's Ratio of the sensing material and the fiber; $\alpha_m$ is the effective coefficient of thermal expansion of each sensing layer 32,34,36; $\alpha_f$ is the coefficient of thermal expansion of the optical fiber 18; $\Delta T$ is the change in temperature by the thermal convective effect; and $\beta$ is thermo-optic coefficient of the fiber material. The first term of equation (2) represents the shift in the Bragg resonant wavelength that is attributable to the interface strain between the sensing layers 32,34,36 and the exterior surface 38 of the optical fiber 18 adjacent to the fiber Bragg gratings 20,22,24, and is proportional to the difference between the coefficients of thermal expansion of the sensing layers 32,34,36 and the fiber material, as well as the thickness 50,52,54 of the sensing layers 32,34,36. Thus, the $\kappa_\epsilon$ coefficient is the strain sensitivity of each respective sensing layer 32,34,36, in terms of the induced shift in the Bragg resonant wavelength of the respective fiber Bragg grating 20,22,24, while $\kappa_T$ coefficient is the temperature sensitivity of each respective fiber Bragg grating. The sum of two coefficients is defined as the thermal sensitivity of each fiber gas sensor (FGS). The second term of equation (2) is indicative of a known shift in the Bragg resonant wavelength that is attributable to the change in temperature $\Delta T$ of the fiber Bragg gratings 20,22,24. Thus, the known shift in the Bragg resonant wavelength is predetermined, and compared with the total shift of the Bragg resonant wavelength, in order to isolate the portion of the shift to the Bragg resonant wavelength which is attributable to the strain of the sensing layer 32,34,36. In addition, the intrinsic elastic strain due to fiber thermal expansion may be too small and its actual effect may be negligible.

In an exemplary embodiment, the fiber gas sensor (FGS) is designed, such that the material and the thickness of each sensing layer 32,34,36 is individually selected, to have a strain sensitivity which is greater than a minimum strain sensitivity $\kappa_\epsilon$ and temperature sensitivity $\kappa K_T$, based on the anticipated temperature change experienced by each sensing layer 32,34,36, in order to induce a response amplitude or shift which is greater than a minimum required response amplitude or shift in the Bragg resonant wavelength, as the gas 12 passes through the hollow chamber 14. In an exemplary embodiment, each sensing layer 32,34,36 may be designed with a respective temperature and strain sensitivity that is tuned to detect a gas within a respective range of heat transfer coefficient. Thus, for example, a first sensing layer 32 may be designed such that the temperature and strain sensitivity of the sensing layer 32 is tuned to detect a gas with a high range of heat transfer coefficient, by inducing a shift in a Bragg resonant wavelength of the fiber Bragg grating 20 which exceeds a threshold required for detection, such as 1 to 10 picometers (pm), for example. In another example, a second sensing layer 34 may be designed such that the strain sensitivity of the sensing layer 34 is tuned to detect a gas with a medium range of heat transfer coefficient, by inducing a shift in a Bragg resonant wavelength of the fiber Bragg grating 22 which exceeds a threshold required for detection, 10 to 50 pm, for example. In another example, a third sensing layer 36 may be designed such that the temperature and strain sensitivity of the sensing layer 36 is tuned to detect a gas within a low range of heat transfer coefficient, by inducing a shift in a Bragg resonant wavelength of the fiber Bragg grating 24 which exceeds a threshold required for detection, 50-100 pm, for example.

As previously discussed, the temperature change in each respective sensing layer 32,34,36 is based on the respective dissipation of heat energy of each sensing layer 32,34,36 with the gas 12, which is in-turn based on the heat transfer coefficient of the gas 12. For example, if a first gas has a high heat transfer coefficient such as a hydrogen (14.38 KJ/kg.K specific heat capacity and 0.168 W/m.K thermal conductivity), this would result in a lower temperature change in the sensing layer 32 because the gas easily absorbs thermal energy from the hollow chamber and warms up the hollow guide and the fiber Bragg gratings, and thus a high strain sensitivity would be required for the material of the sensing layer 32, in order to induce a shift in the Bragg resonant wavelength that is greater than the minimum required shift, such as 1-10 pm, for example. An example of such material with a high coefficient of thermal expansion (CTE) could be Zn, Pb, Sn, and/or Al, for example. As another example, if a second gas has a medium heat transfer coefficient such as methane ($CH_4$) (2.18 KJ/kg.K specific heat capacity and 0.033 W/m.K thermal conductivity), the heat energy dissipation would result in a medium temperature change in the sensing layer 34, and thus only a medium strain sensitivity would be required for the material of the sensing layer 34, in order to yield a shift in the Bragg resonant wavelength that is greater than the minimum required shift, such as 10-50 pm, for example. An example of such material with a medium coefficient of thermal expansion (CTE) could be Ag, Au, and Cu, for example. As another example, if a third gas has a low heat transfer coefficient such as carbon dioxide (0.84 KJ/kg.K specific heat capacity and ~0.015 W/m.K thermal conductivity), the heat energy dissipation would result in a high temperature change in the sensing layer 36, and thus many different materials could be used to integrate with the fiber Bragg grating to form a gas sensor with sufficient thermal sensitivity to induce a shift in the Bragg resonant wavelength that is greater than the minimum required shift, such as 50-100 pm for example. An example of such a material with a low CTE could be Ni, Co and Pd, for example.

Figure 4:
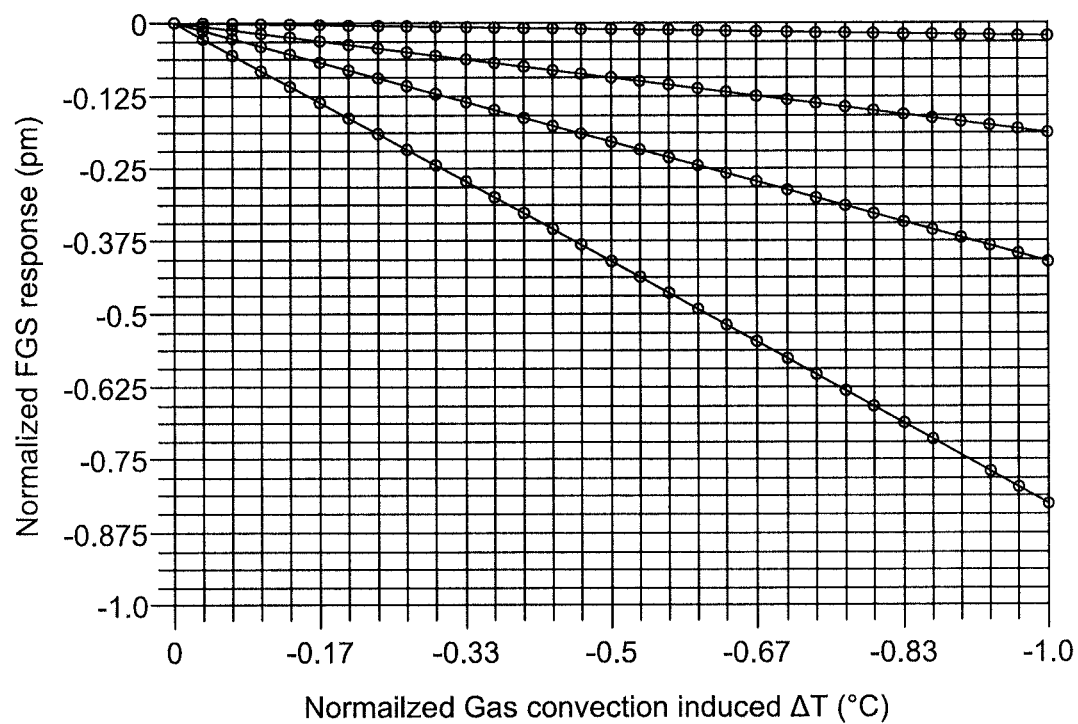
FIG. 4 is a plot of a normalized Bragg resonant wavelength shift versus a normalized temperature change in a sensing layer of varying thickness in the optical sensing fiber illustrated in FIG. 3.

FIG. 4 illustrates a plot of a normalized shift in the Bragg resonant wavelength versus a normalized change in temperature of the respective sensing layer 32,34,36 for varying thickness of a sensing layer material, such as a nickel-based material, for example. The slope of the plot in FIG. 4 is indicative of the fiber gas sensor thermal sensitivity, such as a nickel sensing layer integrated fiber Bragg grating, whose temperature sensitivity is about 11.3 pm/° C. and the strain sensitivity could increase thermal sensitivity of a fiber gas sensor from 11.3 pm/° C. to 16.5 pm/° C., as the thickness of the nickel sensing layer is increased from 0.5 µm to 20 µm, for example. In another example, a different material may be used to be the sensing layer, such as zinc, for example. The thermal sensitivity of a zinc-sensing layer integrated fiber Bragg grating varies from 11.4 pm/° C. to 18.7 pm/° C., as the thickness of the zinc-sensing layer is increased from 0.5 µm to 20 µm, for example. It is clear that the strain effect from the sensing layer could enhance the thermal sensitivity of a fiber gas sensor by 50-60%. For example, for the first gas with the high heat transfer coefficient (e.g., hydrogen, helium), the first sensing layer 32 may be designed to be made from a 20 µm thick zinc material with a strain sensitivity of 18.7 pm/° C. As another example, for the second gas with the medium heat transfer coefficient, the second sensing layer 34 may be designed to be made from a 5 µm thick copper material having a strain sensitivity of 13.3 pm/° C. As another example, for the third gas with the low heat transfer coefficient, the third sensing layer 36 may be designed to be made from a 1 µm thick nickel material having a thermal sensitivity of 11.5 pm/° C. where the strain effect contribution is less than 5%. Thus, the type of material and the thickness of each sensing layer 32,34,36 may be individually tailored, based on the heat transfer coefficient of one or more respective gases, where each respective sensing layer is used to induce the Bragg resonant wavelength shift to identify one or more respective gas(es). Although the above description provides specific numeric wavelength shifts and temperature changes for specific sensing layer materials, the embodiments are not limited to these exemplary sensing layer materials, and include all sensing layer materials and thicknesses, to provide adequate thermal strain sensitivity for a gas or category of gases.

TABLE 1

| Sensing materials | Young's modulus (GPa) | Coefficient of thermal expansion $CTE(10^{-6}/° C.)$ | Poisson's ratio |
| --- | --- | --- | --- |
| Co | 211 | 12.5 | 0.32 |
| Ni | 199.5 | 13.3 | 0.312 |
| Zn | 104.5 | 31 | 0.249 |
| Cu | 129.8 | 17 | 0.343 |
| Al | 70.6 | 23.5 | 0.345 |
| Ag | 83 | 18.9 | 0.37 |
| Au | 78.5 | 14.1 | 0.42 |
| Sn | 49.9 | 23.5 | 0.357 |
| Cr | 279 | 6.5 | 0.21 |
| Pb | 16.1 | 29 | 0.44 |
| Pt | 168 | 8.8 | 0.38 |
| Pd | 121 | 11.8 | 0.39 |

To design a sensing material integrated fiber Bragg grating as a fiber gas sensor (FGS) to have a maximum response amplitude to a gas, the thermal sensitivity of a fiber gas sensor is a combination of: CTE, elastic modulus, and Poisson's Ratio. Specifically, the higher the CTE and Young's modulus, the higher the thermal sensitivity of a fiber gas sensor, while Poisson's ratio has a smaller effect. Table 1 provides some of the materials that could be used as sensing materials. Thus, the coefficient of thermal expansion (CTE) is provided for various types of material which can be used to form each sensing layer 32,34,36. The CTE is indicative of the thermal strain sensitivity of each material. As shown in Table 1, the CTE for zinc is $31 \times 10^{-6}/° C.$, while the CTE for nickel is $13.3 \times 10^{-6}/° C.$, which is consistent with the discussion above that the thermal strain sensitivity of zinc is greater than the thermal strain sensitivity of nickel. Although Table 1 lists the CTE for various materials, the embodiments is not limited to these materials and includes any type of material which can be used to form the sensing layers, such as diamond, diamond-like carbon, and carbides, for example.

Additionally, during a design phase of the sensing module 10, in order to determine the grating locations 26,28,30 within the hollow chamber 14 to position the sensing layers 32,34, 36, an array of temperature sensors, such as thermocouples (not shown) are positioned at incremental locations along the hollow chamber 14. When each gas is passed through the hollow chamber 14 at a fixed flowrate, the temperature sensors detects a temperature of each gas at each location. The grating locations 26,28,30 are determined, based on a location of the temperature sensor at which the respective temperature of each gas has the greatest range/variance. For example, if nitrogen and hydrogen gas are intended to be identified by the sensing module 10, and the temperature sensor determines that the temperature difference between the hydrogen and nitrogen gases is a maximum at a center location of the hollow chamber 14, then a grating location may be selected to coincide with the center location of the hollow chamber 14.

Figure 5:
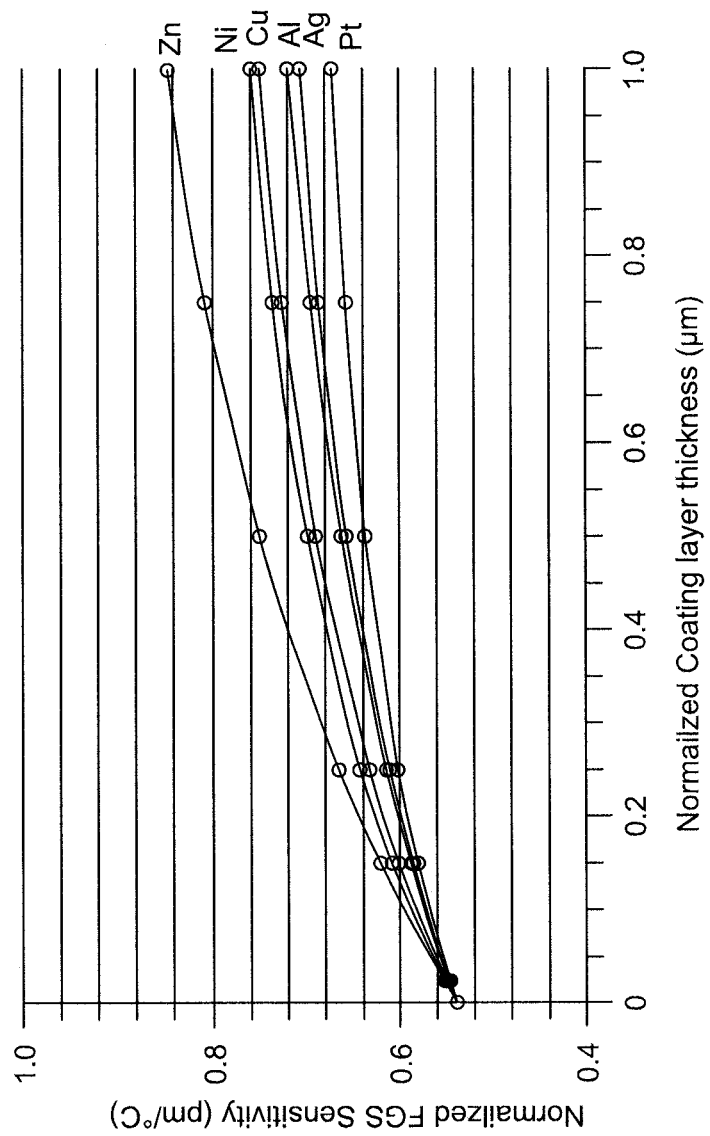
FIG. 5 is a plot of a normalized thermal sensitivity versus a normalized layer thickness of varying materials in the sensing layers illustrated in FIG. 3.

FIG. 5 illustrates a plot of a normalized thermal sensitivity of the sensing layer 32,34,36, with the integrated fiber Bragg gratings 20,22,24, versus the normalized thickness of the sensing layer 32,34,36, as the thickness of the sensing layer 32,34,36 is increased, for different types of sensing layer materials. Thus, as discussed above with regard to the CTE and elastic modulus in Table 1, the type of material used to form the sensing layer 32,34,36 affects the thermal sensitivity of the fiber gas sensor due to the strain effect, with the same thickness. Additionally, as illustrated in FIG. 5, the thermal sensitivity of each fiber gas sensor increases, as the thickness of the sensing layer is correspondingly increased.

Figure 6:
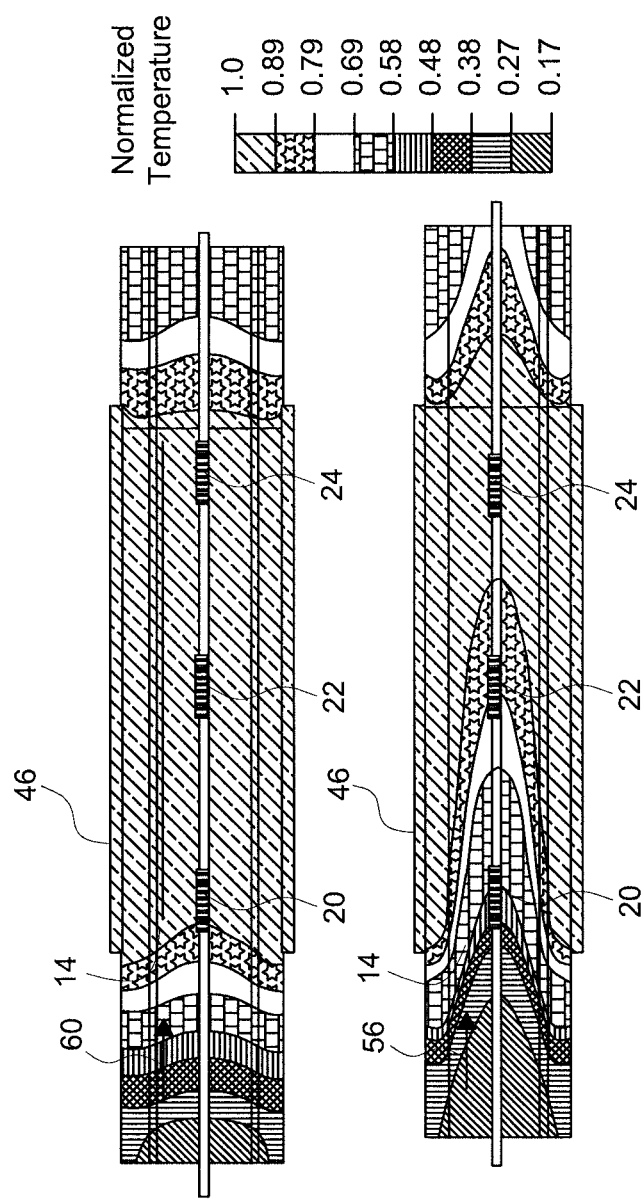
FIG. 6 is a partial-side cross-sectional view of the thermal profile inside the sensing module illustrated in FIG. 2, showing a normalized scaled temperature within the sensing module for two gases with different specific heat capacities.

FIG. 6 illustrates a temperature-contour view of the fiber gas sensor in the hollow chamber, in which the normalized temperature within the hollow chamber 14 is provided by a grey-scale. The first sensing layer 32 is designed with a high strain sensitivity, to induce the Bragg resonant wavelength shift in response to a gas 60 with a convective effect within a range of a high heat transfer coefficient, and the second sensing layer 34 is designed with a sufficient strain sensitivity, to induce the Bragg resonant wavelength shift in response to a gas 56 with a convective effect within a range of low heat transfer coefficient. For example, the top view of FIG. 6 illustrates the thermal contour of the fiber Bragg grating 20,22,24 in the hollow chamber 14, in response to the gas 60 convective effect within the range of high heat transfer coefficient, such as hydrogen gas, for example. The high heat transfer coefficient of the hydrogen gas can easily carry away the thermal energy from both the sensing layers 32,34,36 and the hollow chamber 14. In this thermal dynamic process, the gas 60 stream can absorb heat energy from the hollow chamber 14 relatively quickly, and thus has induced a relatively small change in the temperature of the fiber Bragg grating 20, and an even smaller change in the temperature of the fiber Bragg gratings 22,24 along the hollow guide length.

Accordingly, the first sensing layer 32, which is designed to detect the gas 60 with the high heat transfer coefficient, is designed with a high strain sensitivity (i.e., high thermal expansion characteristic and/or higher thickness) to induce the shift in the Bragg resonant wavelength that is characteristic of the high heat transfer coefficient, where the induced shift in the Bragg resonant wavelength is greater than a threshold shift required for detection, 1-10 pm for example. Contrastingly, the bottom view of FIG. 6 illustrates the thermal contour of the fiber gas sensors in the hollow chamber 14, in response to the gas 56 with a low heat transfer coefficient, such as carbon dioxide, for example. The low heat transfer coefficient of the carbon dioxide gas has absorbed less of the thermal energy from the hollow chamber 14 but easily absorbs thermal energy from the sensing layers 32,34,36, compared to the hydrogen gas in the top view, and thus has induced a relatively larger change in the temperature of the sensing layers 32,34,36. Accordingly, the second sensing layer 34, which is designed to detect the gas 56 with the low heat transfer coefficient, is designed with a low to medium strain sensitivity (i.e., low to medium CTE, elastic modulus, and/or less than 10 µm thickness) to induce the response amplitude or shift in the Bragg resonant wavelength that is characteristic of gas with the low heat transfer coefficient where the induced shift in the Bragg resonant wavelength is greater than a threshold shift required for gas detection.

As previously discussed, the sensing module 10 includes the process unit or photodetector 112 to detect the respective shift in the Bragg resonant wavelength from each respective fiber Bragg grating 20,22,24 or fiber gas sensors. Additionally, the sensing module 10 includes the processor or controller 114 coupled to the process unit 112, to operate in either a calibration/pulse mode or an identification/continuous mode. In the identification mode, the processor 114 identifies the gas 12 within the hollow chamber 14, based on a comparison of the detected response amplitude or shift in the Bragg resonant wavelength (received from the process unit 112) with a predetermined shift in the Bragg resonant wavelength for a plurality of known gases. However, before the sensing module 10 is used to identify the gas 12, the processor 114 is switched into the calibration mode, during which the predetermined Bragg resonant wavelength shifts for each known gas is stored in the memory of the processor 114. As discussed above, the sensing module 10 includes a flowmeter 11 which adjustably varies the flowrate at which the gas 12 flows through the hollow chamber 14. During the calibration mode, a first type of calibration or baseline determination of a gas involves passing a known gas through the hollow chamber 14 at varying flowrates. Specifically, a known gas is separately directed into the hollow chamber 14 at a number of different flowrates by adjusting the flowmeter 11. As the known gas passes through the hollow chamber 14, the thermal exchange between the known gas and the sensing layers 32,34,36 induces the shift in the Bragg resonant wavelength of each respective fiber Bragg grating 20,22,24, which is detected and stored in the memory of the processor 114, for each respective flowrate and fiber Bragg grating 20,22,24. Subsequently, when the processor 114 is switched into the identification mode, and the test gas 12 passes through the hollow chamber 14, the processor 114 identifies the gas 12 by comparing the detected shift of the Bragg wavelength with each stored shift of the Bragg resonant wavelength for each known gas at each respective flowrate. For example, hydrogen may induce a 100 pm downshift for a flowrate of 500 standard cubic centimeters per minute (sccm), while a binary mixture of air and carbon dioxide may induce a 300-1100 pm downshift at the same flowrate.

Figure 7:
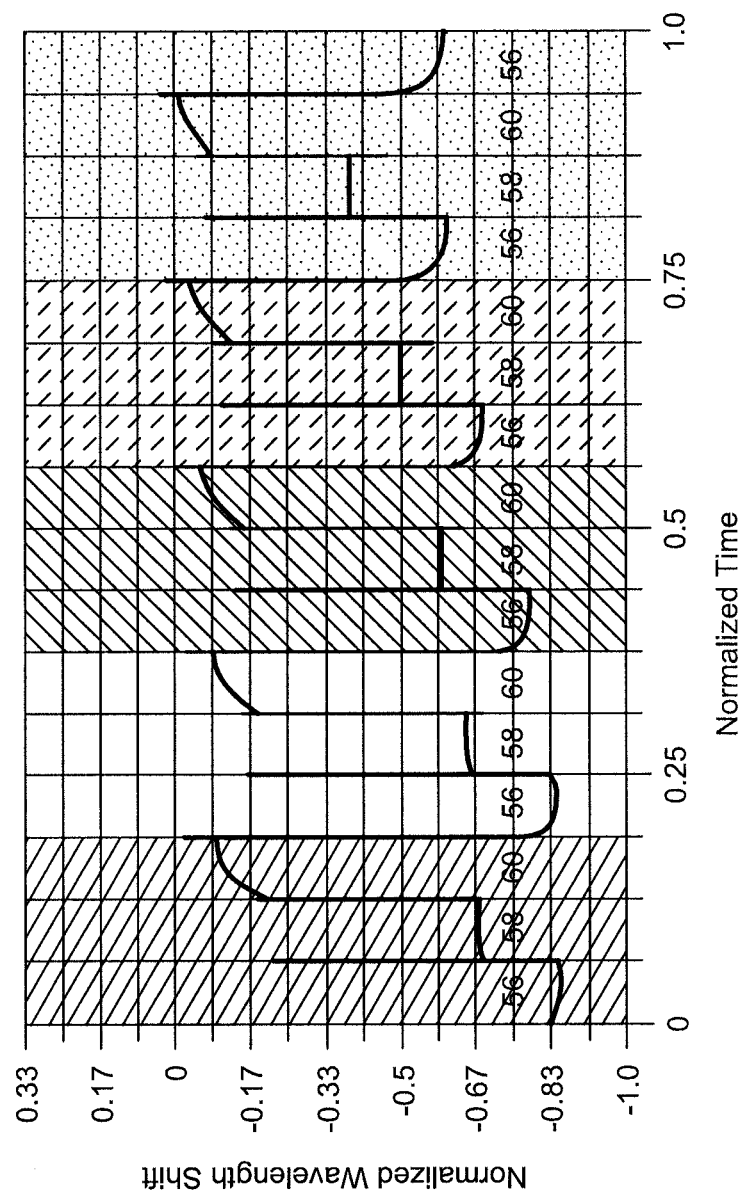
FIG. 7 is a plot of a normalized Bragg resonant wavelength shift versus normalized time, for a variety of gases and flowrates passing through the sensing module illustrated in FIG. 2.

Additionally, during the calibration mode, a second calibration or baseline determination of a gas involves multiple gases which are individually passed into the hollow chamber 14 at a fixed flowrate. The shift in the Bragg resonant wavelength is measured and stored in the memory of the processor 114 for each respective gas at the fixed flowrate. Subsequently, in the identification mode, the processor 114 identifies the gas 12 based on the comparison of the detected shift of the Bragg resonant wavelength with each stored shift of the Bragg resonant wavelength for each respective gas at the fixed flowrate. FIG. 7 illustrates the results of both calibration or baseline determination techniques discussed above, and the resulting stored normalized shifts of the Bragg resonant wavelength in the memory of the processor 114. Using the first calibration for the first gas 56, the calibration mode yielded a normalized shift in the Bragg resonant wavelength of −0.57 (−700 pm), −0.67 (−800 pm), −0.80 (−950 pm), −0.83 (−1000 pm), and −0.85 (−1050 pm) for the respective flowrates of 500 sccm, 600 sccm, 700 sccm, 800 sccm and 900 sccm. In an exemplary embodiment, the temperature of the thermal stabilizer is set to 140° C. (284° F.), and the shift of the Bragg resonant wavelength from the second fiber Bragg grating 22 or fiber gas sensor is used. However, the calibration mode is not limited to this experimental setup, and may utilize various temperature settings of the thermal stabilizer 46, as well as various Bragg gratings 20,22,24 or fiber gas sensors to measure the shift in the Bragg resonant wavelength. Using the second calibration for a first gas 56, a second gas 58 and a third gas 60 at a fixed flowrate of 900 sccm, the calibration mode yielded a respective normalized shift in the Bragg resonant wavelength of −0.85 (−1050 pm), −0.67(−800 pm) and −0.15(−150 pm), respectively. In an exemplary embodiment, the first gas 56, the second gas 58 and the third gas 60 are carbon dioxide, pure nitrogen gas and pure hydrogen gas, for example. Although FIG. 7 provides calibration data for specific gases, the embodiments is not limited to these specific gases, and includes the collection of calibration data for any gas to be identified by the sensor system.

Although FIG. 7 illustrates the results of the calibration mode, including the response amplitudes with various single-component pure gases in an alternatively cycling test with three gases, the sensing module 10 is not limited to the identification of pure gases, and includes the identification of binary gases and multi-component gases. Thus, the calibration or pulse mode of the processor 114 includes the use of a known single-component pure gas, two-component binary gas (with a known concentration of multiple pure gases), or even a multi-component multi-gas, and passing the known gas mixture into the hollow chamber 14 at a fixed flow rate. As with the pure gas calibration, the shift in the Bragg resonant wavelength is measured and stored in the memory of the processor 114 for the known concentration of the known binary gas. These steps are repeated for each concentration of the binary gas or multi-gas which may be subject to identification by the sensing module 10, and are repeated for each binary gas or multi-gas which may be subject to identification by the sensing module 10.

Figure 8:
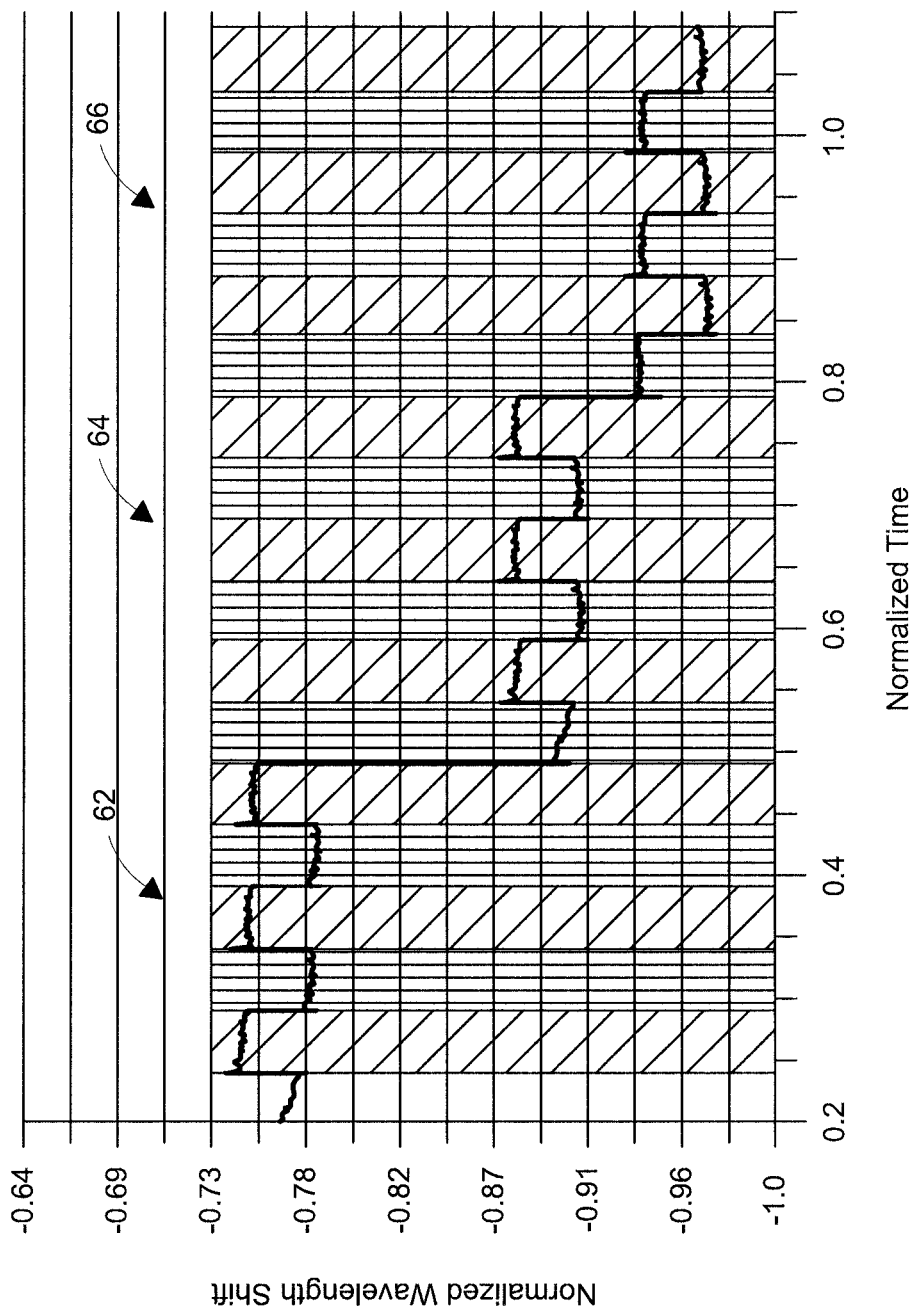
FIG. 8 is a plot of a normalized Bragg resonant wavelength shift versus normalized time, for a variety of concentrations of a binary gas passing through the sensing module illustrated in FIG. 1.

Subsequently, in the identification mode, the processor 114 identifies the concentration of a gas composition which is passed into the hollow chamber 14, based on a comparison of the detected shift of the Bragg resonant wavelength of the binary gas or multi-gas with each stored Bragg resonant wavelength shift for each respective concentration of all known gases at the fixed flow rate. FIG. 8 illustrates an exemplary embodiment of the results of the calibration of the shifts in the normalized Bragg resonant wavelength for a binary or a multi-gas. In an exemplary embodiment, one setup used to obtain the calibration data of FIG. 8 involves setting the temperature of the thermal stabilizer 46 to 140° C. (284° F.), and fixing the flowrate of the various concentrations of the binary gas at 600 sccm. However, the embodiments are not limited to this specific experimental setup and may vary the temperature of the thermal stabilizer 46, and/or the flowrate of the binary gas or multi-gas through the hollow chamber 14. Specifically, the shift in the Bragg resonant wavelength for a first concentration 62, second concentration 64 and third concentration 66 is measured for a known binary or multi gas, at a fixed flowrate. In an exemplary embodiment, the known binary gas is $H_2+CO_2$, and the concentrations are 9-10% $H_2$ in 90-91% $CO_2$ (first concentration); 5-6% $H_2$ in 94-95% $CO_2$ (second concentration); and 3-4% $H_2$ in 96-97% $CO_2$ (third concentration). Although FIG. 8 illustrates specific normalized calibration data for a specific binary gas, the embodiments are not limited to this specific binary gas, and include the collection of calibration data for any binary gas which is to be identified by the gas detection system. In an exemplary embodiment, the normalized Bragg resonant wavelengths from this binary gas calibration may be used to identify the concentration of gas mixture from a generator case in a generator, before the generator is opened, to make sure that the relative concentration of hydrogen gas is less than 5%, for example.

As discussed above, after the gas 12 passes through the hollow chamber 14, it exits the sensing module 10 through the outlet 27. Based on the thermal dissipation of heat energy from the sensing layers 32,34,36 to the gas 12, the temperature of the sensing layers 32,34,36 is reduced from the initial operation temperature to a thermal stabilized status. In an exemplary embodiment, the fiber Bragg grating 20 may induce a relatively large wavelength downshift, the fiber Bragg grating 22 may induce a relatively medium wavelength downshift, and the fiber Bragg grating 24 may induce a relatively small wavelength downshift. Such thermal response dynamics is determined by the hollow chamber 14 thermal contours, which are used to identify gas compositions when the sensing material has no chemical sensitivity. After the gas 12 has exited the hollow chamber 14 and the outlet 27, the thermal stabilizer 46 maintains the sensing module 10 thermal stability to a new thermal equilibrium status that is in-between the first and second temperatures. In the pulse/calibration mode, and during the operation of the sensing module 10 when no gas is flowing through the chamber 14, the sensing layers 32,34,36 temperature will return to the operation temperature or first temperature, before a subsequent gas is introduced into the hollow chamber 14 for gas identification.

Figure 9:
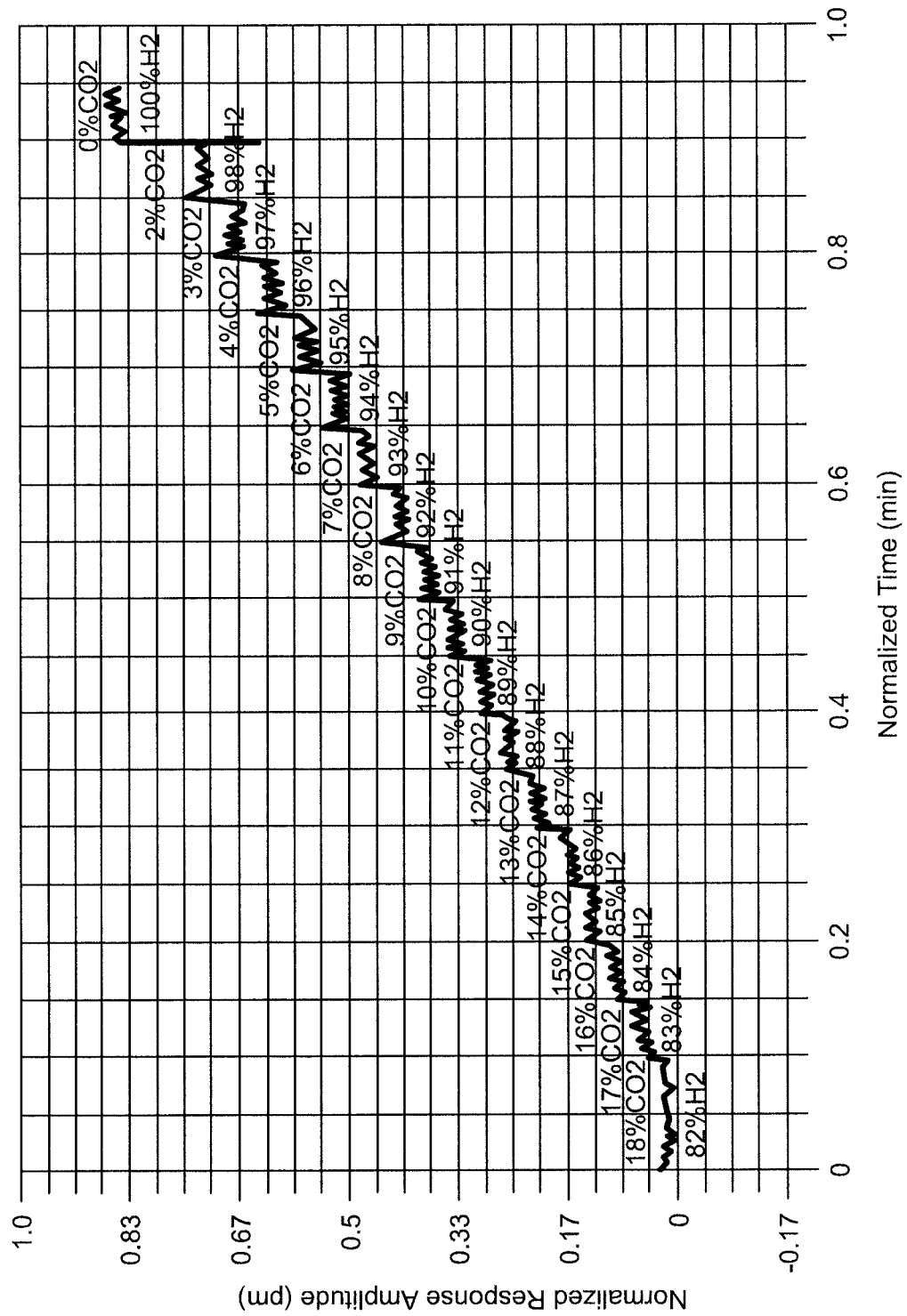
FIG. 9 is a plot of a normalized Bragg resonant wavelength shift versus time, for a variety of varying gases passing through the sensing module illustrated in FIG. 2 in accordance with aspects of the present invention.

FIG. 9 illustrates a plot similar to FIG. 8, with the exception that the binary gas has a relatively high concentration of hydrogen gas and a relatively low concentration of carbon dioxide. Additionally, as illustrated in FIG. 9, the concentration of the binary gas is varied by increments of 1%, after which the sensing module 10 measures the shift in the Bragg resonant wavelength from the fiber Bragg gratings 20,22,24. As illustrated in FIG. 9, the concentration range of the binary gas varies from 18% Carbon Dioxide in 82% Hydrogen up to 0% Carbon Dioxide in 100% Hydrogen, in 1% increments (i.e., reduce Carbon Dioxide by 1% and increase Hydrogen by 1%). The sensing module 10 is capable of measuring the wavelength shift of the Bragg resonant wavelength for these increments in the binary gas. For example, the binary concentration mixture of 6% Carbon Dioxide in 94% Hydrogen results in a Bragg resonant wavelength shift of 30 pm, while the binary concentration mixture of 5% Carbon Dioxide in 95% Hydrogen results in a Bragg resonant wavelength shift of 33 pm detected by the system 100, for example. FIG. 9 is merely exemplary and the embodiments are not limited to the relative concentration ranges for Carbon Dioxide/Hydrogen depicted in FIG. 9, nor the numerical wavelength shifts represented in the plot. Thus, the results displayed in FIG. 9 may be similarly produced for any kind of binary gas mixture composition analysis.

While various embodiments of the present invention have been shown and described herein, it will be apparent that such embodiments are provided by way of example only. Numerous variations, changes and substitutions may be made without departing from the invention herein. Accordingly, it is intended that the invention be limited only by the spirit and scope of the appended claims.

What is claimed is:

1. A gas detection system for identifying at least one of a plurality of gases, comprising:
   at least one sensing module including:
      a hollow chamber enclosed by a chamber housing;
      an optical sensing fiber positioned within the hollow chamber, said optical sensing fiber comprising a plurality of fiber gas sensors including,
         a plurality of fiber Bragg gratings which are spaced apart at a plurality of respective grating locations along the fiber, and
         a respective sensing layer affixed to an exterior surface of the optical fiber at each respective grating location, wherein at least one sensing layer of at least one fiber gas sensor is configured with a thermal sensitivity tuned to detect a first gas and a second gas having respective first and second heat transfer coefficients, said first heat transfer coefficient being greater than said second heat transfer coefficient,
      wherein a first material is selected for the at least one sensing layer of a first fiber Bragg grating at a first grating location and a second material is selected for the sensing layer of a second fiber Bragg grating at a second grating location, the first and second materials have respective first and second thermal expansion characteristics and respective first and second thicknesses, where the first thermal expansion characteristic is greater than the second thermal expansion characteristic and the first thickness is greater than the second thickness,
      wherein the first material is configured to dissipate heat energy to the second gas when said second gas is directed into the hollow chamber based at least in part on the second heat transfer coefficient of the second gas, said dissipation of heat energy to induce strain in said at least one sensing layer and in the first fiber Bragg grating sufficient to induce a shift in the Bragg resonant wavelength of the first fiber Bragg grating which is greater than a threshold shift required for detection of the second gas, said strain is based on at least one of the first thermal expansion characteristic and the first thickness of the first material,
      wherein the second material is configured to dissipate heat energy to the first gas when said first gas is directed into the hollow chamber based at least in part on the first heat transfer coefficient of the first gas, said dissipation of heat energy to induce strain in said sensing layer and in the second fiber Bragg grating sufficient to induce a shift in the Bragg resonant wavelength of the second fiber Bragg grating which is greater than a threshold shift required for detection of the first gas, said strain is based on at least one of the second thermal expansion characteristic and the second thickness of the second material; and
   a photodetector configured to detect said respective shift in the Bragg resonant wavelength for each fiber gas sensor.

2. The gas detection system of claim 1, wherein said at least one sensing module further includes a thermal stabilizer attached to an exterior surface of the chamber housing and configured to maintain temperatures of said at least one sensing layer and said optical fiber at a first temperature in the absence of said at least one gas.

3. The gas detection system of claim 2, further comprising a gas injection mechanism configured to direct said first and second gases into the hollow chamber at an initial second temperature, said second temperature being different than the first temperature; and wherein said dissipation of the heat energy is based on a temperature difference between the second temperature and the first temperature, and first and second heat transfer coefficients of the respective first and second materials.

4. The gas detection system of claim 2, wherein the temperature of the at least one sensing layer and the at least one fiber gas sensor is reduced from the first temperature, based on the dissipation of the heat energy;
   and wherein upon the gas exiting the hollow chamber, the thermal stabilizer is configured to re-heat the at least one fiber gas sensor and the hollow chamber to the first temperature, to baseline the at least one fiber gas sensor before another gas is directed into the hollow chamber.

5. The gas detection system of claim 1, wherein the hollow chamber includes a sensing rake within a hollow guide and the chamber housing includes a double-wall cylindrical housing, said cylindrical housing made from a material with a thermal expansion characteristic based on a thermal expansion characteristic of the optical sensing fiber.

6. A gas detection system for identifying at least one of a plurality of gases, comprising:
   an optical sensing fiber including a plurality of gas sensors, each gas sensor including a respective fiber Bragg grating positioned at a grating location along the optical sensing fiber, and a respective sensing layer affixed to an exterior surface of the optical fiber at the grating location, wherein at least one sensing layer of at least one gas sensor is configured with a thermal sensitivity tuned to detect a first gas and a second gas having respective first and second heat transfer coefficients, said first heat transfer coefficient being greater than said second heat transfer coefficient,
   wherein a first material is selected for the at least one sensing layer of a first fiber Bragg grating at a first grating location and a second material is selected for the sensing layer of a second fiber Bragg grating at a second grating location, the first and second materials have respective first and second thermal expansion characteristics and respective first and second thicknesses, where the first thermal expansion characteristic is greater than the second thermal expansion characteristic and the first thickness is greater than the second thickness,
   wherein the first material is configured to dissipate heat energy to the second gas based at least in part on the second heat transfer coefficient of the second gas, said dissipation of heat energy to induce strain in said at least one sensing layer and in the first fiber Bragg grating sufficient to induce a shift in the Bragg resonant wavelength of the first fiber Bragg grating which is greater than a threshold shift required for detection of the second gas, said strain is based on at least one of the first thermal expansion characteristic and the first thickness of the first material,
   wherein the second material is configured to dissipate heat energy to the first gas based at least in part on the first heat transfer coefficient of the first gas, said dissipation of heat energy to induce strain in said sensing layer and in the second fiber Bragg grating sufficient to induce a shift in the Bragg resonant wavelength of the second fiber Bragg grating which is greater than a threshold shift required for detection of the first gas, said strain is based on at least one of the second thermal expansion characteristic and the second thickness of the second material; and
   a photodetector configured to detect said respective shift in the Bragg resonant wavelength for each gas sensor.

7. The gas detection system of claim 6, wherein said gas detection system includes at least one sensing module, said sensing module comprising:
   a hollow chamber including a chamber housing, said first gas or said second gas being directed into the hollow chamber at a flowrate;
   wherein said gas sensors are positioned within the hollow chamber; and
   wherein said second material is configured to dissipate the heat energy to the first gas based on a temperature difference between said sensing layer and the first gas, and said first material is configured to dissipate the heat energy to the second gas based on a temperature difference between said at least one sensing layer and the second gas.

8. A gas detection system for identifying a gas, comprising:
   a hollow chamber enclosed by a chamber housing, said hollow chamber configured to receive the gas;
   an optical sensing fiber positioned within the hollow chamber, said optical sensing fiber including a plurality of gas sensors, each gas sensor including a respective fiber Bragg grating positioned at a respective grating location along the optical sensing fiber;
   a respective sensing layer affixed to an exterior surface of the optical sensing fiber at each grating location, wherein said sensing layer of the gas sensor and said gas are configured to exchange heat energy when said gas is directed into the hollow chamber based at least in part on a heat transfer coefficient of the gas, said exchange of the heat energy is configured to induce a shift in a Bragg resonant wavelength of the fiber Bragg grating of the gas sensor which exceeds a identify the gas;
   a thermal stabilizer attached to an exterior surface of the chamber housing and configured to maintain temperatures of said sensing layer and said optical sensing fiber at a first temperature in the absence of said gas, wherein the temperature of the at least one sensing layer and the at least one fiber gas sensor is reduced from the first temperature, based on the exchange of the heat energy between said sensing layer and said gas, and wherein upon the gas exiting the hollow chamber, the thermal stabilizer is configured to re-heat the gas sensor and the hollow chamber to the first temperature, to baseline the gas sensor before another gas is directed into the hollow chamber; and
   a photodetector configured to detect said shift in the Bragg resonant wavelength for the gas sensor.

9. A gas detection system for identifying a gas, comprising:
   a hollow chamber enclosed by a chamber housing, said hollow chamber configured to receive the gas, wherein the hollow chamber includes a sensing rake within a hollow guide and the chamber housing includes a double-wall cylindrical housing, said cylindrical housing made from a material with a thermal expansion characteristic based on a thermal expansion characteristic of an optical sensing fiber,
   wherein the optical sensing fiber is positioned within the hollow chamber, said optical sensing fiber including a plurality of gas sensors, each gas sensor including a respective fiber Bragg grating positioned at a respective grating location along the optical sensing fiber;
   a respective sensing layer affixed to an exterior surface of the optical sensing fiber at each grating location, wherein said sensing layer of the gas sensor and said gas are configured to exchange heat energy when said gas is directed into the hollow chamber based at least in part on a heat transfer coefficient of the gas, said exchange of the heat energy is configured to induce a shift in a Bragg resonant wavelength of the fiber Bragg grating of the gas sensor which exceeds a threshold shift required for detection, said shift in the Bragg resonant wavelength to be used to identify the gas; and
   a photodetector configured to detect said shift in the Bragg resonant wavelength for the gas sensor.

* * * * *

UNITED STATES PATENT AND TRADEMARK OFFICE
CERTIFICATE OF CORRECTION

PATENT NO. : 8,542,955 B2  
APPLICATION NO. : 12/913950  
DATED : September 24, 2013  
INVENTOR(S) : Xia et al.

Page 1 of 1

It is certified that error appears in the above-identified patent and that said Letters Patent is hereby corrected as shown below:

In the Specifications

In Column 9, Line 8, delete "$\lambda_\beta$" and insert -- $\lambda_B$ --, therefor.

In Column 9, Line 45, delete "$\kappa K_T$," and insert -- $\kappa_T$, --, therefor.

In the Claims

In Column 18, Line 22, in Claim 8, delete "exceeds a" and insert -- exceeds a threshold shift required for detection, said shift in the Bragg resonant wavelength to be used to --, therefor.

Signed and Sealed this  
Twenty-second Day of April, 2014

Michelle K. Lee  
*Deputy Director of the United States Patent and Trademark Office*